US010952715B2

(12) United States Patent
Hunt et al.

(10) Patent No.: US 10,952,715 B2
(45) Date of Patent: *Mar. 23, 2021

(54) SURGICAL RETRACTOR SYSTEM AND METHODS OF USE

(71) Applicant: NuVasive, Inc., San Diego, CA (US)

(72) Inventors: Leonel A. Hunt, San Diego, CA (US); Gabriel E. Hunt, San Diego, CA (US); Drew Schifle, San Diego, CA (US); Greg Causey, San Diego, CA (US); Alan Burkholder, San Diego, CA (US)

(*) Notice: Subject to any disclaimer, the term of this patent is extended or adjusted under 35 U.S.C. 154(b) by 66 days.

This patent is subject to a terminal disclaimer.

(21) Appl. No.: 16/237,247

(22) Filed: Dec. 31, 2018

(65) Prior Publication Data
US 2019/0209152 A1 Jul. 11, 2019

Related U.S. Application Data

(63) Continuation of application No. 14/239,528, filed as application No. PCT/US2012/051480 on Aug. 17, 2012, now Pat. No. 10,166,018.

(60) Provisional application No. 61/532,751, filed on Sep. 9, 2011, provisional application No. 61/525,646, filed on Aug. 19, 2011.

(51) Int. Cl.
A61B 17/02 (2006.01)
A61B 17/28 (2006.01)
A61B 17/00 (2006.01)

(52) U.S. Cl.
CPC ........ A61B 17/025 (2013.01); A61B 17/0206 (2013.01); A61B 17/282 (2013.01); A61B 2017/0092 (2013.01); A61B 2017/00915 (2013.01); A61B 2017/0256 (2013.01); F04C 2270/0421 (2013.01)

(58) Field of Classification Search
CPC ... A61B 17/02; A61B 17/0206; A61B 17/025; A61B 17/0256; A61B 17/0262
USPC .......................... 600/214, 219, 221, 222, 228
See application file for complete search history.

(56) References Cited

U.S. PATENT DOCUMENTS

| 5,928,139 A | 7/1999 | Koros et al. |
| 5,944,658 A | 8/1999 | Koros et al. |
| 7,207,949 B2 | 4/2007 | Miles et al. |
| 7,582,058 B1 | 9/2009 | Miles et al. |
| 7,691,057 B2 | 4/2010 | Miles et al. |
| 7,819,801 B2 | 10/2010 | Miles et al. |
| 7,905,840 B2 | 3/2011 | Pimenta et al. |
| 8,137,284 B2 | 3/2012 | Miles et al. |
| 8,251,997 B2 | 8/2012 | Michelson |

(Continued)

OTHER PUBLICATIONS

International Preliminary Report on Patentability and Written Opinion for PCT/US2012/051480, ISA, dated Mar. 6, 2014.

(Continued)

Primary Examiner — Matthew J Lawson

(57) ABSTRACT

A surgical retractor includes an elongate element defining an operational axis, a first blade secured to the elongate element and comprising a blade face, a second blade moveably secured to the elongate element, wherein the second blade defines a reference point located thereon, and wherein a movement of the second blade moves the reference point in a linear direction parallel to the operational axis and orthogonal to the blade face. A guide element may be removably located within an opening located on either the first blade or the second blade.

18 Claims, 9 Drawing Sheets

(56) References Cited

U.S. PATENT DOCUMENTS

| | | |
|---|---|---|
| 8,313,430 B1 | 11/2012 | Pimenta |
| 8,449,463 B2 | 5/2013 | Nunley et al. |
| 9,486,133 B2 | 11/2016 | Lee et al. |
| 2001/0037123 A1 | 11/2001 | Hancock |
| 2002/0147387 A1 | 10/2002 | Paolitto et al. |
| 2005/0277812 A1 | 12/2005 | Myles |
| 2008/0146885 A1 | 6/2008 | Protopsaltis |
| 2008/0221394 A1 | 9/2008 | Melkent et al. |
| 2009/0036746 A1* | 2/2009 | Blackwell .......... A61B 17/0206 600/219 |
| 2010/0174146 A1 | 7/2010 | Miles et al. |
| 2011/0046448 A1 | 2/2011 | Paolitto et al. |

OTHER PUBLICATIONS

International Search Report for PCT/US2012/051480, ISA, dated Oct. 29, 2012.

* cited by examiner

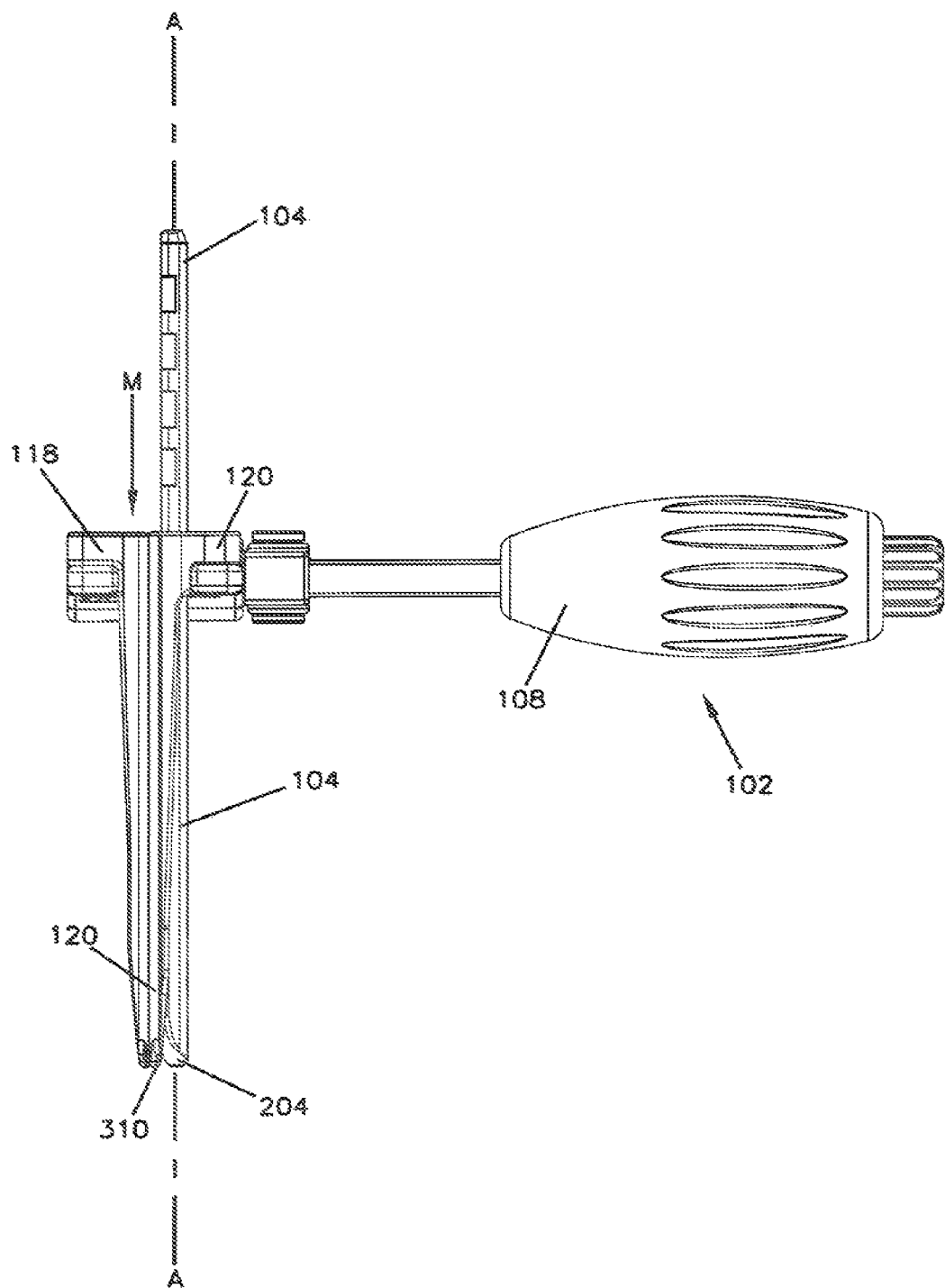

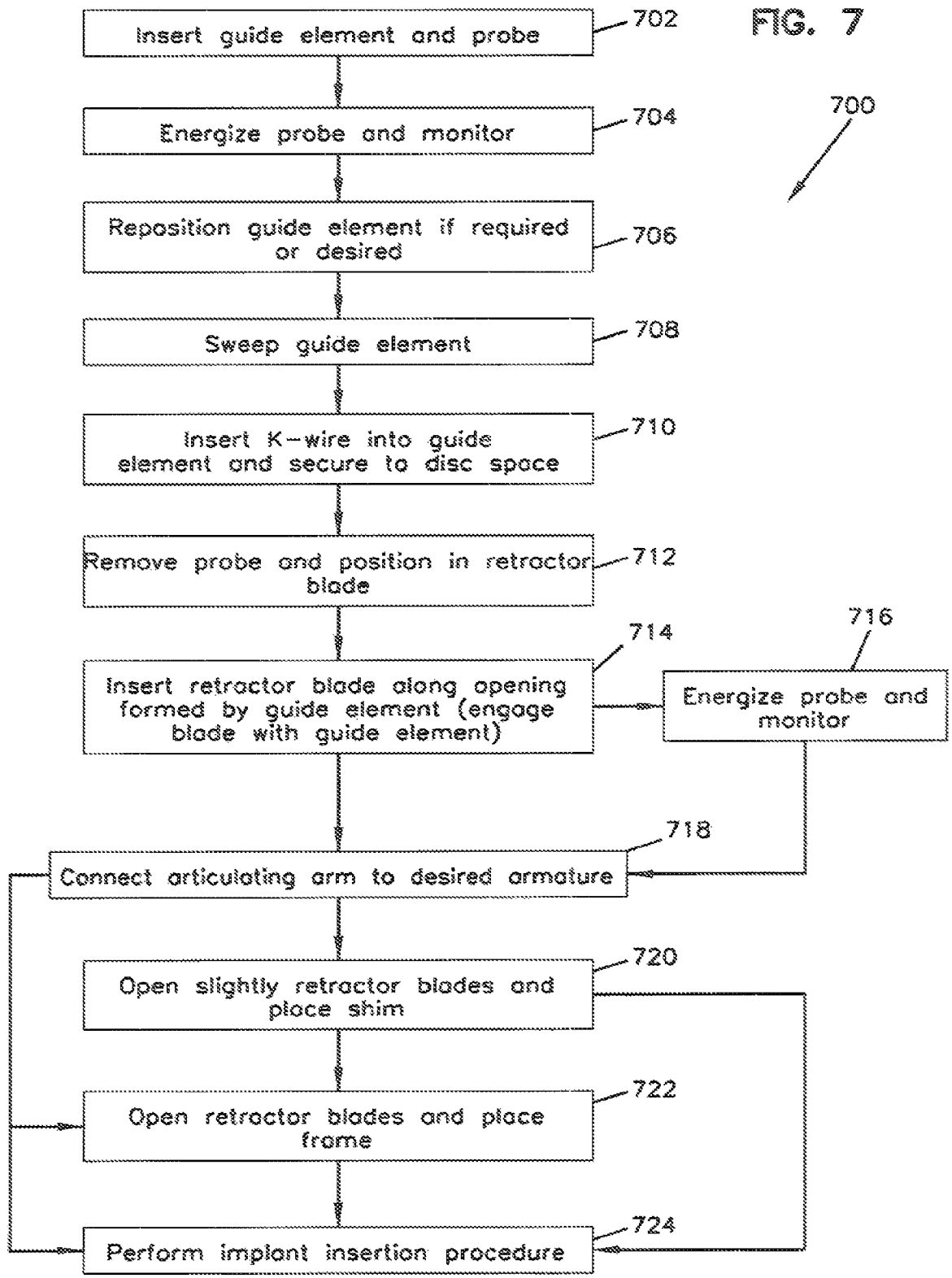

SURGICAL RETRACTOR SYSTEM AND METHODS OF USE

CROSS-REFERENCE TO RELATED APPLICATIONS

This application claims priority to and the benefit of U.S. Provisional Application Ser. No. 61/525,646, filed Aug. 19, 2011, entitled, "Surgical Retractor System and Methods of Use"; and U.S. Provisional Application Ser. No. 61/532,751, filed Sep. 9, 2011, entitled, "Surgical Retractor System and Methods of Use"; the disclosures of which are hereby incorporated by reference herein in their entireties.

INTRODUCTION

Current retractor systems for lateral spine surgical procedures create a round opening through the psoas muscle, which includes muscle fibers running mostly in the cranial-caudal direction. These systems use sequentially inserted round dilators which dilate the surgical site radially away from the initial dilator/K-wire insertion point, which can lead to compression of nerves and blood supply on the transverse process of the vertebral body. Existing retractor systems include the ability to monitor the most posterior point of each instrument being entered into the psoas, but continue to introduce larger instruments into the area of concern. These previous systems also typically include two, three, or four round dilators that must first be forced into the muscle tissue before the retractor can be inserted around the largest dilator. These round dilators, coupled with multi-blade retractors that spread radially, can cause significant muscular trauma, and can further stretch or compress nerve roots in the surrounding tissue.

SUMMARY

In one aspect, the technology relates to surgical retractors and methods of use. In one embodiment, a surgical retractor includes an elongate element defining an operational axis. A first blade, having a first blade face, is secured to the elongate element. A second blade defining an opening is moveably secured to the elongate element and defines a reference point thereon. Movement of the second blade moves the reference point in a linear direction generally parallel to the operational axis and generally orthogonal to the blade face. A guide element is removably received within the opening.

In another embodiment, a method of performing spinal surgery using a lateral approach includes inserting a guide element into a first location above a target surgical site, and repositioning the guide element into a second location above the target surgical site. The second location may be more posterior than the first location. The method includes inserting a retractor device along the guide element, with the retractor device having first and second retractor blades that are inserted along only a first side of the guide element. The first retractor blade is anchored to the target surgical site. The method includes separating the first and second retractor blades by moving the second retractor blade away from the first retractor blade, and locking the first and second retractor blades to maintain an open access to the target surgical site.

It is to be understood that both the foregoing general description and the following detailed description are exemplary and explanatory and are intended to provide further explanation of the technology as claimed.

BRIEF DESCRIPTION OF THE DRAWINGS

There are shown in the drawings, embodiments which are presently preferred, it being understood, however, that the technology is not limited to the precise arrangements and instrumentalities shown.

FIGS. 3A and 3B depict a top view and a side view, respectively, a retractor device.

FIG. 7 depicts a method of using a retractor system.

DETAILED DESCRIPTION

Figure 1:
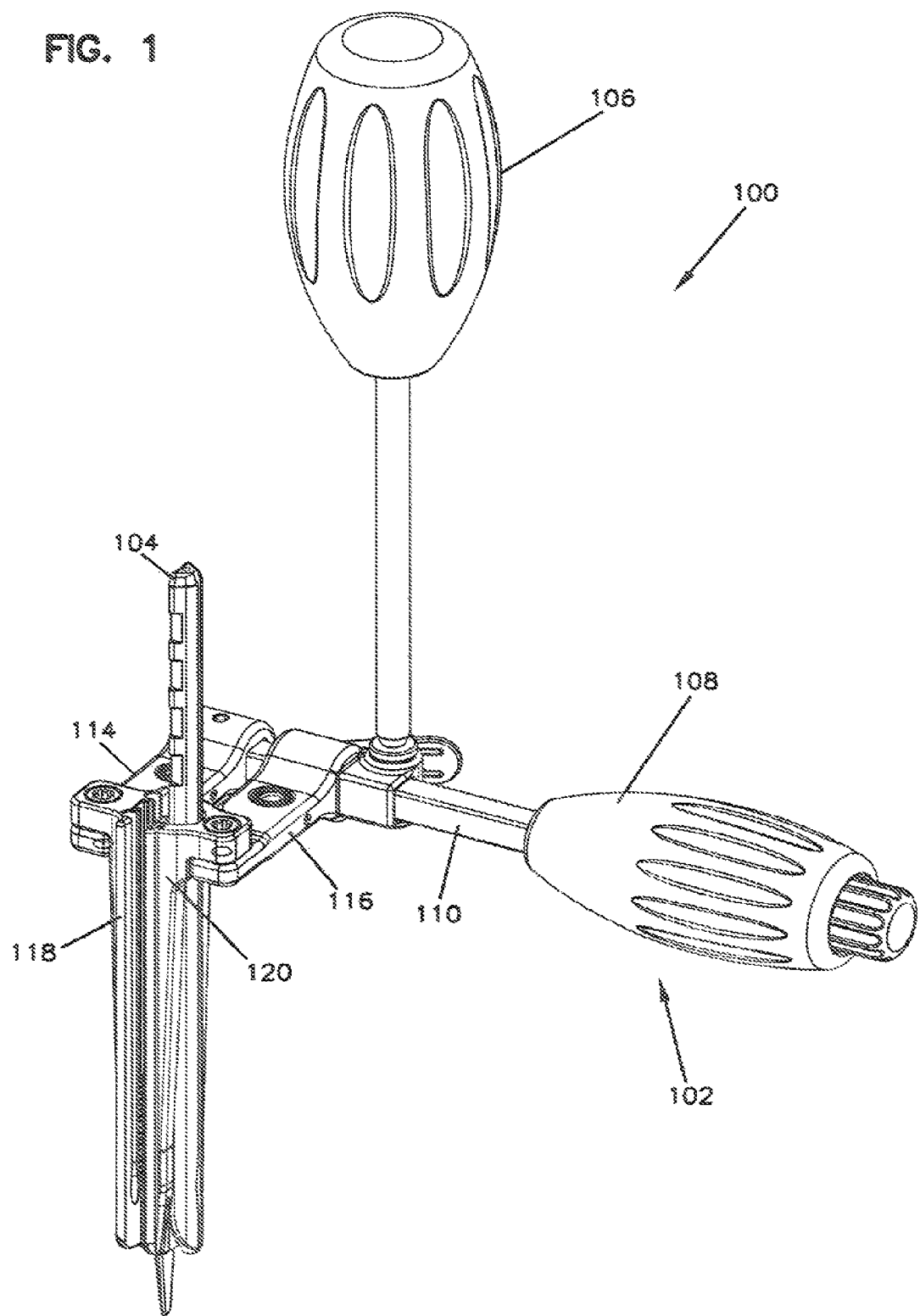
FIG. 1 depicts a perspective view of a retractor system.

FIG. 1 depicts a retractor system 100 that includes, generally, a retractor device 102, a guide element 104, and a driver 106. The retractor device 102 includes a handle 108 coupled to an elongate element 110 to which two blades 118, 120 are secured. In some embodiments, the handle 108 is a removable handle that is selectively coupled to or removed from the elongate element 110. The blades 118, 120 may be secured directly to the elongate element 110 or secured with one or more armatures 114, 116. As shown in FIG. 1, in one embodiment, the armatures 114, 116 extend from a side of the elongate element 110, such that a surgical opening created by the blades 118, 120 may be accessible by the surgeon performing the operation without obstruction by the elongate element 110. One or both of the armatures 114, 116 may be movably secured to the elongate element 110. In this particular embodiment, the driver 106 is used to actuate a moving mechanism, in this case, to rotate a gear that engages with a rack along the elongate element 110. Actuation of the moving mechanism can operate to separate the armatures 114, 116, and thus separate the blades 118, 120. This mechanism is more clearly depicted in FIG. 3B. Other moving mechanisms may be used to move the blades 118, 120 relative to the elongated elements. For example, lead screw/nut mechanisms and linear rail/slide mechanisms may be used. Certain of these systems may require additional locking elements, as described below. One of the retractor blades 118, 120 (in one embodiment, the posterior blade 120) defines an opening for receipt of the elongate guide element 104, the use of which is described below. Additionally, one or both of the blades 118, 120 may be configured to removably receive one or more shims.

Figure 2:
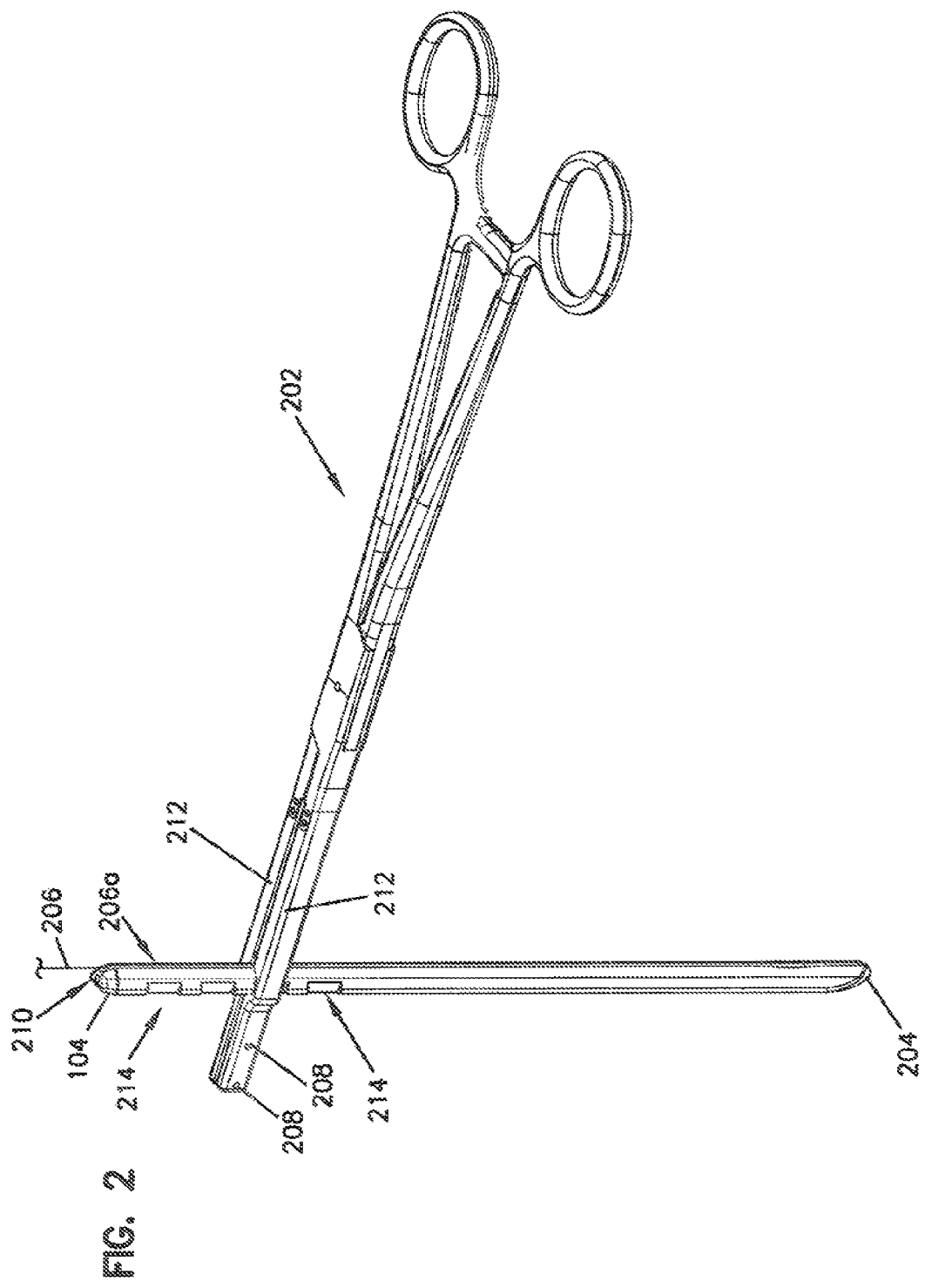
FIG. 2 depicts perspective views of a guide element insertion device.

The guide element 104 and a guide element insertion device 202 are depicted in FIG. 2. In the depicted embodiment, the guide element 104 is an elongate dissector having a generally D-shaped profile, although the present disclosure contemplates other elongated dissector profile shapes, including elliptical, trapezoidal, oblong, triangular, and the like. The blunt tip 204 and profile shape of the guide element 104 simplifies the insertion process and also assists in splitting the psoas along the plane of the muscle fibers. A probe 206 may be placed in a channel 206a or opening extending lengthwise along the guide element 104. After insertion, once a desired position is confirmed, a K-wire can be placed via the same or a second channel to dock the guide element 104 to the disc space. In an alternative embodiment, the K-wire may be already inserted into the guide element 104, prior to the guide element 104 being inserted. An opening, bore, or channel 210 in the guide element 104 sized to receive the K-wire, and discrete from the probe channel, is depicted in FIG. 2. This opening 210 may be a fully closed channel, a partially closed channel, or some combination thereof. Depending on the embodiment, the K-wire channel 210 may be located in or on the guide element 104 (as shown), in armature 114 or armature 116, or in an anterior retractor blade 118 or a posterior retractor blade 120.

The guide element 104 may include a number of notches 214 that provide an engagement surface for an insertion device 202. In the depicted embodiment, forceps including radio-lucent arms 212 are used for insertion. Other types of insertion devices may be used, or the guide element 104 may also be positioned by hand, if desired. The radio-lucent forceps arms 212 typically will not show during fluoroscopy, but radio-opaque markers 208 may be included on the arms 202 to assist in positioning. Radio-opaque markers 208 placed at other locations indicating the positions/locations of certain elements may be utilized. Additionally, the guide element 104 may also be radio-lucent. Radio-opaque markers also may be positioned proximate the center and anterior border of an implant to be inserted during the surgical procedure.

Figure 3B:
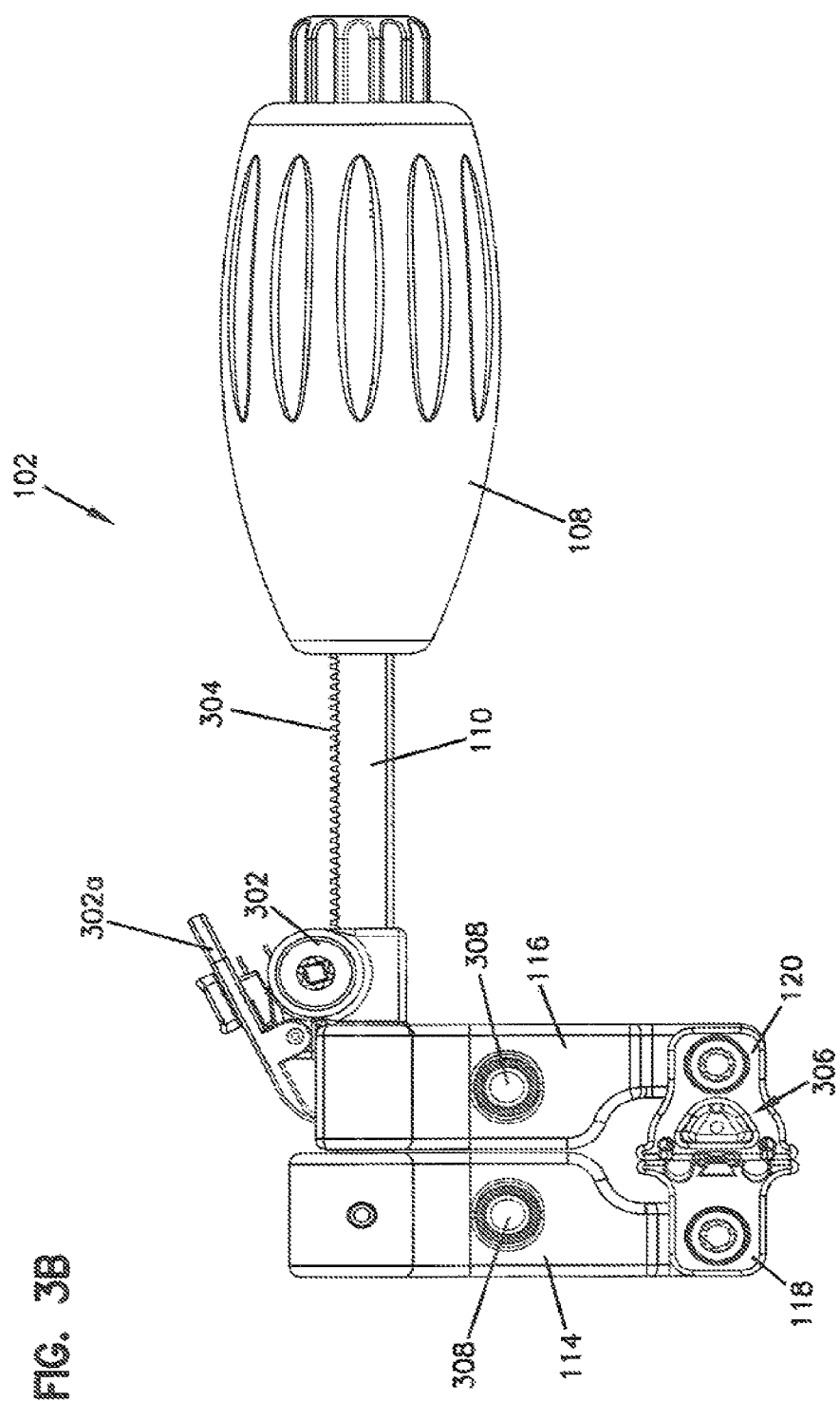

FIGS. 3A-3B depict various views of a dissector-type guide element 104 used in conjunction with a retractor device 102. As initially described above, the driver is used to actuate a moving mechanism, in this case, to rotate a gear 302 that engages with a rack 304 along the elongate element 110. A locking element 302a a may prevent further movement of the gear when engaged, by for example, engaging the rack 304. The guide element 104 is received within an opening 306 defined by at least one of the retractor blades 118, 120. In the depicted embodiment, the opening 306 is located in the posterior blade 120. Alternatively or additionally, an opening 306 may be located in the anterior blade 118 or in either or both of the armatures 114, 116. Once the guide element 104 is inserted into the skin surface and muscle tissue to a desired depth, the retractor device 102 is moved M along an axis A so as to receive the guide element 104 in the opening 306. As most readily seen in FIG. 3B, the flat portion of the generally D-shaped guide element 104 is facing anteriorly (i.e., towards the blades 118, 120), such that the retractor device 102 is slid over the guide element 104 with the face surfaces of the opposing retractor blades 118, 120 facing each other. Since the guide element 104 is located in the opening 306 defined in the exterior surface of the posterior blade 120, all or substantially all of both blades 118, 120 are located on the same side of the guide element 104, unlike dilator/retractor systems that locate the blades 118, 120 on both sides of (or around) dilators. FIG. 3A depicts a distal end 310 of the posterior retractor blade 120, along with the guide element 104 located along a rear surface of the blade 120. In general, the distal ends 310 of the retractor blades 118, 120 should not be inserted lower than the tip 204 of the guide element 104, but the blades 118, 120 may be inserted further, if desired.

FIG. 3B also depicts the retractor lock 302a, which is used to fix the position of the posterior blade armature 116 along the elongate element 110 and to prevent inadvertent movement of the armature 116, and therefore the blade 120, along the elongate element 110. In this case, the retractor lock 302a may be disengaged prior to rotating the gear 302 with the driver 106, as described above in the context of FIG. 1. The retractor lock 302a then may be reengaged to prevent further movement of the armature 116. The retractor lock 302a may engage with the elongate element 110, either at the rack 304 itself or at a separate point located on the elongate element 110. Each armature 114, 116 includes an articulating arm connection 308, such as that described below. Once the retractor blades 118, 120 are inserted into the psoas muscle, an articulating arm (not shown) may be connected to either the anterior blade armature 114 or the posterior blade armature 116. An opposite end of the articulating arm is connected to a fixed point (typically on the operating table), to hold the retractor device 102 in position during operation of the opening mechanism. When the articulating arm is connected to the anterior blade armature 114, actuation of the opening mechanism will move the posterior blade 120 along the elongate element 110, towards the handle 108. When the articulating arm is connected to the posterior blade armature 116, actuation of the opening mechanism will move the anterior blade 118 in a direction away from the posterior blade 120. Note that in this second configuration, since the posterior blade armature 116 is connected to the elongate element 110, each of the anterior blade 118, its armature 114, the elongate element 110, and the handle 108 move relative to the fixed posterior blade 120 as the opening mechanism is operated. Depending on the location of the guide element 104 and desired position of the surgical corridor, an operator may make the articulating arm connection 308 as desired. It should be noted that by fixing the position of the posterior blade 120 with the articulating arm, the possibility of compressing nerves and/or restricting the blood flow due to pressure on the transverse process is reduced or eliminated. The two-blade, flat-blade design assists in splitting the psoas muscle along the plane of the muscle fibers, thereby reducing trauma.

It should also be noted that either or both of the blades 118, 120 may be configured with any number of openings, channels, or other structures that allow for receipt of an electrode probe, such that the location of nerves may be determined during insertion of the retractor device 102, during opening of the blades 118, 120, or after opening of the blades 118, 120. Use of such probes for identifying nerve proximity and direction is well-known within the field of spinal surgery, and will not be further described herein. Additionally, the same or other channels may be used to hold a light source used to illuminate the surgical corridor.

Figure 4:
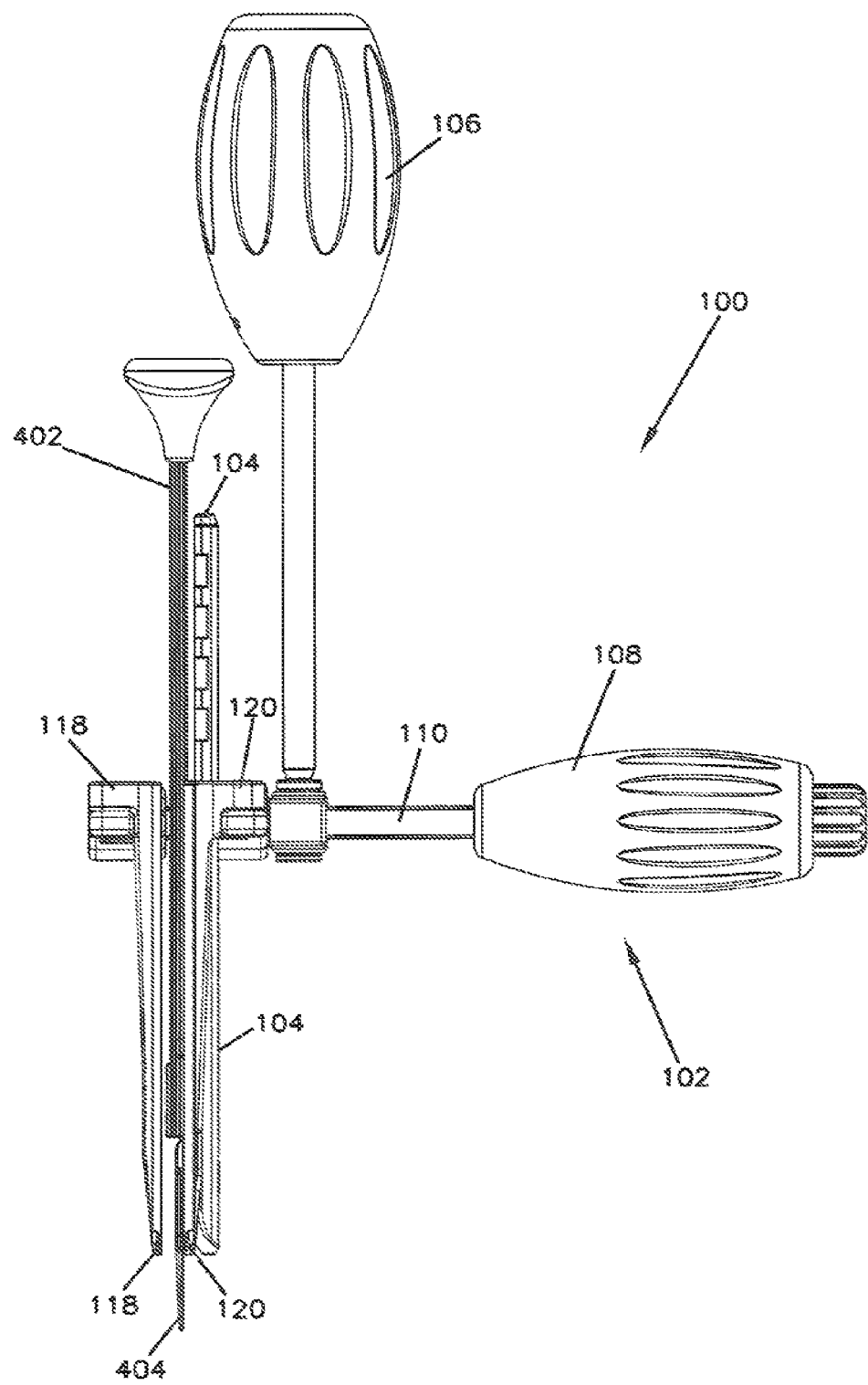
FIG. 4 depicts a side view of a retractor system.
Figure 5B:
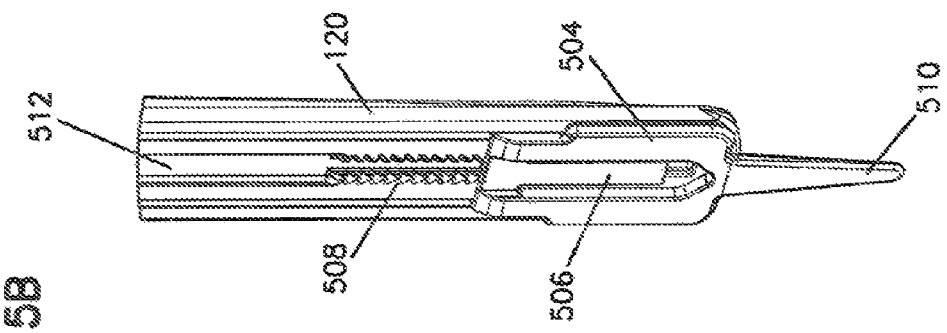
FIGS. 5A and 5B depict enlarged partial perspective views of a retractor blades.
Figure 5A:
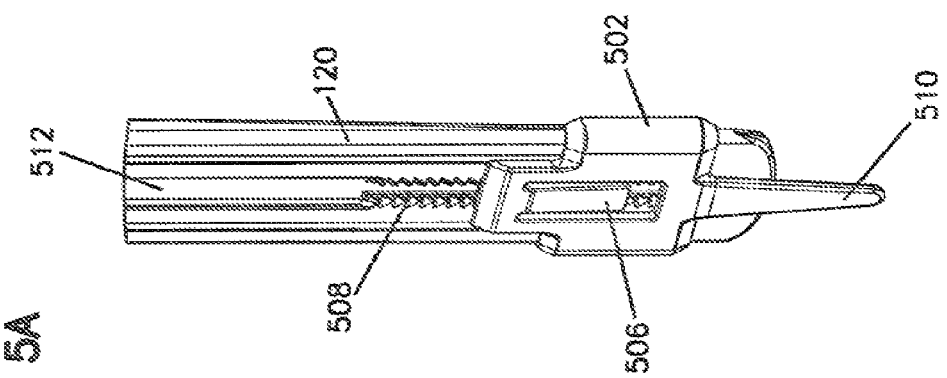

FIG. 4 depicts a partial side view of the retractor system 100. In some embodiments, the retractor blades 118, 120 of the device may be fitted with one or more shims that serve particular purposes during surgery. Widening shims may be used to help ensure muscle tissue does not encroach on the surgical corridor. Lengthening shims may be used to effectively lengthen the depth of penetration of the blades 118, 120. Intradiscal shims may be used to penetrate the disc space of the spine so as to access the disc and hold one of the blades 118, 120 of the retractor device 102 in place, relative to the spine. As depicted in FIG. 4, the anterior blade 118 and the posterior blade 120 may be separated slightly so as to allow access to the space between with a shim inserter 402, which is used to guide a shim 404 down to the appropriate location along the blade. FIGS. 5A and 5B depict a wrap-around shim 502 and an internally-confined shim 504, respectively. Either shim 122 type may be used in conjunction with the retractor device 102, on either or both of the anterior blade 118 and the posterior blade 120. Once the shim(s) are installed, it may be desirable to remove either or both of the K-wire and the guide element 104 prior to opening the retractor blades 118, 120 to the desired maximum position. Either shim 502, 504 may include a ratchet 506 that engages with a rack 508 located on the blade 120, such that the shim 502, 504 may be inserted to a desired depth and held in place. Both of the shims 502, 504 depicted in FIGS. 5A and 5B are intradiscal shims that include a tip 510 that may be inserted into the disc space, to help fix the location of the blade 120 internal to the body. The rack 508 may extend along a portion of an inner channel 512 of the blade 118, 120, or may extend the entire length of the inner channel 512.

Figure 6A:
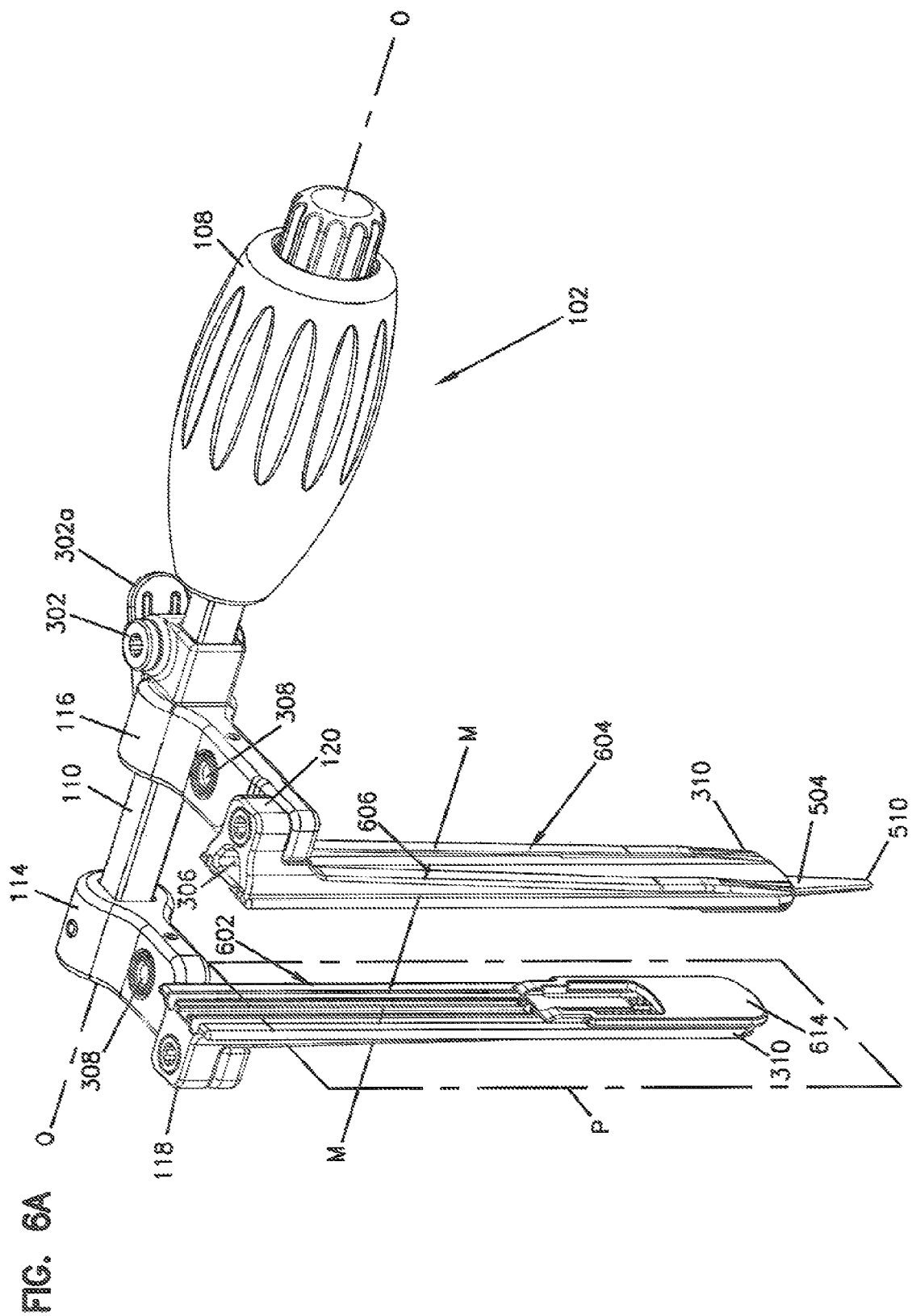
FIGS. 6A and 6B depict perspective views of a retractor device.
Figure 6B:
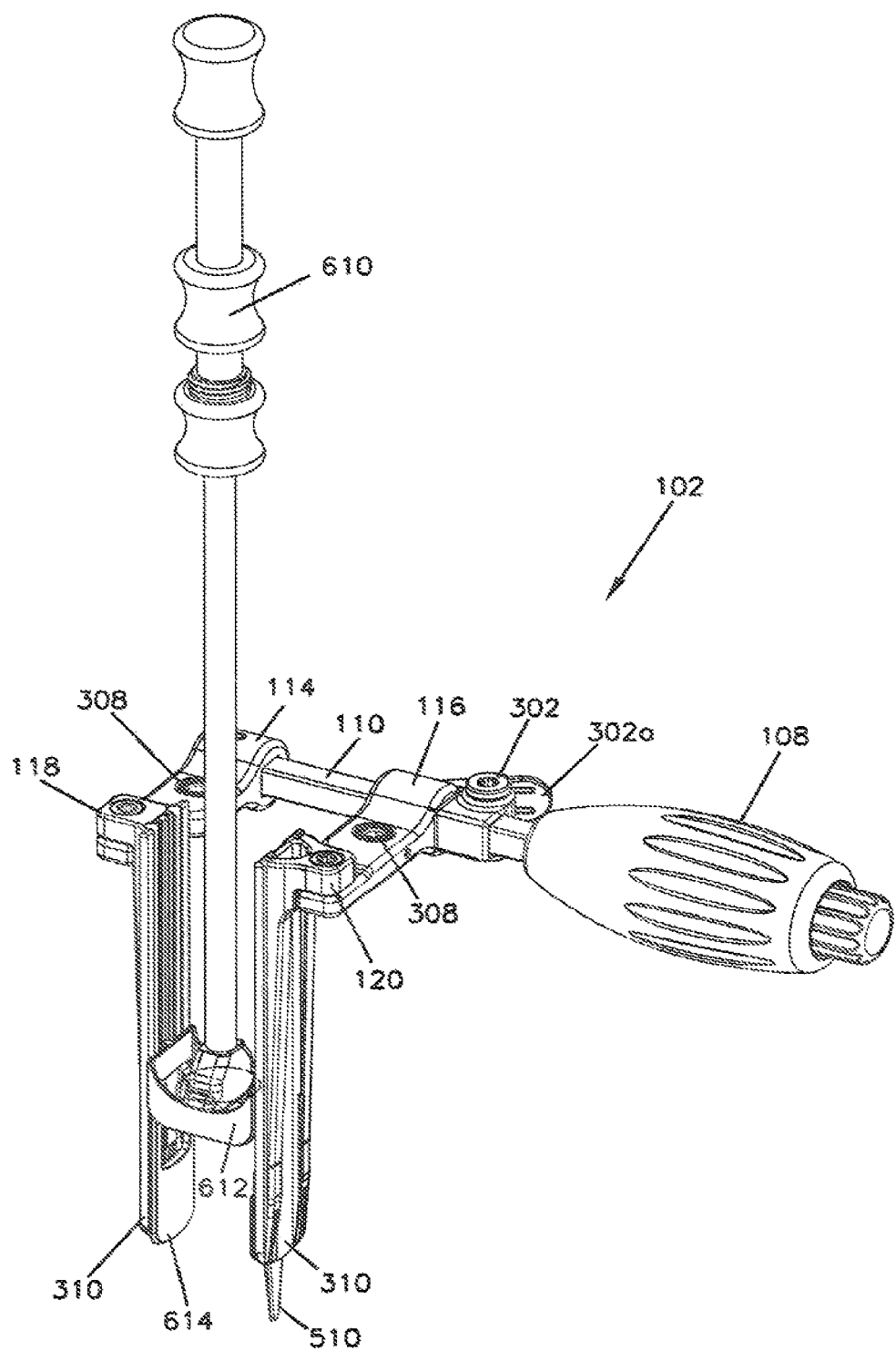

FIGS. 6A-6B depict the embodiment of the retractor device 102 shown in an open position, creating a surgical corridor within the muscle tissue. Of course, a functional surgical corridor need not require the blades 118, 120 to be opened to a maximum distance. If desired or required, a frame 612 may be placed between the blades 118, 120 to provide support to the distal ends 310 of the blades 118, 120. This may be useful, for example, should the surrounding tissue force an inward deflection of the blade ends 310 and thus cause a narrowing of the surgical corridor. The frame 612 may be held in place via the inner channels 512 located in either or both of the blades 118, 120, and may be inserted with an insertion element 610 (e.g., a pair of forceps). FIGS. 6A and 6B also depict a lengthening shim 614 located on the anterior blade 118.

Movement of the blade relative to the elongate element 110 is described with reference to FIG. 6A. The elongate element 110 defines an operational axis O. Each front face of the anterior blade 118 and the posterior blade 120 define a plane. For clarity, only anterior plane P is depicted in FIG. 6A. Each of the blades 118, 120 also includes a reference point 606 located thereon. The reference point 606 may be located on the face surface 602 or rear surface 604 of the blade, or may be a defined point thereon, for example, a center of gravity, a blade tip, a radio-opaque reference point, etc. Additionally, the reference point 606 need not be a distinct physical point. Instead, that term is used herein to further define movement of the blades 118, 120. Regardless, a predetermined reference point 606 is identified on the rear surface 604 of the posterior blade 120 in FIG. 6A. For the purposes of this example, the articulating arm described above is connected to the anterior blade armature 114. Therefore, as the moving mechanism (the gear 302) is operated, the posterior blade 120 moves toward the handle 108. In that regard, the reference point 606 moves along an axis of movement M that is generally parallel to the operational axis O and generally orthogonal to the anterior blade plane P. This configuration of axes and planes, as well as the substantially flat configuration of the blades 118, 120, helps ensure muscular separation along the muscle fiber plane, thereby limiting muscular trauma. Of course, if the articulating arm is connected to the posterior blade armature 116, similar movement of the anterior blade 118 occurs. A reference point located on the anterior blade 118 moves along an axis generally parallel to the operational axis O, as well as generally orthogonal to the posterior blade plane. Also, if the articulating arm is connected to the posterior blade armature 116, the intradiscal shim 504 depicted may be inserted into the intradiscal space to help further limit movement of the posterior blade 120. In general, the tip 510 of the intradiscal shim 504 is not extended beyond the blade tip 310 during movement of the blade 118, 120 on which the intradiscal shim 504 is installed.

FIG. 7 depicts a method 700 of using a retractor system in a surgical procedure. Although the method is described in the context of lateral-approach spinal surgery, it should be noted that the systems and methods described herein may be used in virtually any surgery where limited muscular and/or nerve trauma is desired. In surgeries where limited, controlled separation of muscle fibers is desirable, the retractor system described herein may be particularly advantageous.

Further, while shown in FIG. 7 as a series of operations, method 700 can combine operations or eliminate operations altogether. For example, operations related to nerve monitoring and probes may be omitted in the event the surgeon does not elect to use nerve monitoring. Initially, a guide element is inserted (operation 702) into the area of interest (in this case, the psoas muscle) and directed toward the target tissue, organ, or skeletal structure (in this case a vertebrae or disc space). An electrode probe may be located in the guide element prior to insertion and introduced at the same time as the guide element. The probe may then be energized and the feedback monitored (operation 704) to check for nerve response (e.g., in the lumbar plexus). In certain surgeries, the guide element is positioned so as to be centered near the anterior one-third of the intravertebral disc. The guide element may be repositioned (operation 706) as required or desired, generally until a suitable location is found. Electrode monitoring (operation 704) may be repeated to confirm the location is safe for the surgery to continue. In a particular embodiment, the guide element is repositioned (operation 706) posteriorly in small increments until the desired location is found and nerve monitoring indicates the location is safe for surgery to continue. In a particular embodiment, the guide element is positioned as far posterior as possible, so that subsequent retractor blade movement will be a movement of only the anterior blade away from the posterior blade.

Once the proper position is confirmed, the guide element may be swept (operation 708) side-to-side so as to create a plane in the psoas muscle and make an initial opening into which a retractor device will be inserted. Thereafter, a K-wire may be inserted (operation 710) via the guide element toward the target region, and secured relative to the disc space. Prior to insertion of the retractor device, the monitoring probe may be removed (operation 712) from the guide element and inserted into one of the retractor blades. This would allow for monitoring of nerve response during insertion of the retractor, which may be desirable in certain situations. Alternatively, a second monitoring probe may be used with the retractor. Due to the unique configuration of the retractor system, the retractor blades are inserted on the same side of the guide element, into the opening formed by the earlier sweeping movement thereof. As described above, this helps separate the psoas muscle along the muscle fibers. Additionally, by inserting both blades on the same side of the guide element, the guide element can be positioned on the posterior side of the desired surgical site, with the posterior blade also being positioned on the posterior side of the desired surgical site.

As the retractor device is inserted (operation 714) into the initial surgical opening, the guide element is inserted into the opening defined by the retractor blade, typically the posterior retractor blade. After inserting the retractor blade a certain distance into the muscle, the probe may be energized and the feedback monitored to confirm location and/or proximity of the blades relative to nearby nerves (operation 716). This blade position monitoring operation 716 need not be performed however. Regardless, once the retractor blades reach their desired depth of penetration, an articulating arm may be connected (operation 718) to either of the posterior blade armature and the anterior blade armature. As described above, connection to either of the armatures will dictate which of the armatures moves and, accordingly, the direction of separation of the retractor blades, (i.e., anteriorly or posteriorly). Once secured to the armature, a number of different actions may be taken in virtually any order to complete the surgical procedure. For example, the blades may be spread slightly and a shim may be inserted (operation 720). A shim may accomplish any of the purposes described above, and in one embodiment is used to further anchor the distal end of one of the blades to help secure it place relative to a desired surgical site. Thereafter or alternatively, the blades may be spread further and a frame may be inserted (operation 722) to provide rigidity to the distal ends of the retractor blades. Again, this blade separation may occur from just a single blade moving while the other blade remains generally in place. At any point, desired surgical procedures may be performed (operation 724), such as a partial or full discectomy, and insertion of an implant per the surgeon's discretion. Of course, surgical procedures may be performed at any time after insertion of the blades, and the shims and/or the frame may be inserted at any time during the procedure, as required. For example, if a surgical procedure is initiated without insertion of a frame, but during the procedure, the surgical corridor begins to contract, the surgeon may then insert the shim and/or the frame. Additionally, the looking mechanism may be locked and unlocked as required during the procedure.

Materials utilized in the manufacture of the retractor system may be those typically used in surgical equipment. Stainless steel, titanium, and other robust metals that may be sterilized may be used. In applications where fluoroscopy is desirable or required during the procedure (e.g., in the spinal surgery procedures described herein), radio-lucent materials may be particularly desirable. In those applications, aluminum, anodized aluminum, and rigid polymers may be utilized. Carbon fiber-reinforced polymers may be particular useful, as they are lightweight, extremely strong, and may be sterilized. Of course, retractor systems utilizing a combination of materials may be used. For example, radio-lucent materials may be used for the blades and less expensive radio-opaque material may be utilized for the elongate element and armatures. Additionally, radio-lucent materials may be impregnated in discrete locations with radio-opaque materials such that position of certain parts of the system may be visible during procedures, without impeding overall visibility.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the technology. Accordingly, what is desired to be secured by Letters Patent is the technology as defined and differentiated in the following claims, and all equivalents.

What is claimed is:

1. A surgical retractor comprising:
    an elongate element comprising an elongate element distal end and an elongate element proximal end with a length therebetween, the elongate element defining an operational axis along the length thereof,
    a retractor handle secured to the elongate element proximal end;
    a first blade having a first upper portion secured to a first arm extending from the elongate element distal end and a first blade portion comprising a first blade face;
    a second blade having a second upper portion secured to a second arm extending from the elongate element and a second blade portion having a second blade face that faces the first blade face, wherein the second arm is positioned along the length of the elongate element at a position between the retractor handle and the first arm, the second arm configured to move along the length of the elongate element, wherein the second blade defines a reference point located thereon, and wherein a movement of the second arm along the length of the elongate element moves the reference point in a linear direction parallel to the operational axis and orthogonal to the second blade face, wherein movement of the second arm along the length of the elongate element moves the second arm relative to the retractor handle and relative to the first arm, wherein the second blade further comprises an opening along a length of the second blade and through the second upper portion, wherein the opening of the second blade is dimensioned to receive a guide element therethrough such that surgical retractor is advanceable to a surgical target site with the first blade portion and second blade portion located on the same side of the guide element.

2. The surgical retractor of claim 1, further comprising means for moving the second blade relative to the elongate element.

3. The surgical retractor of claim 2, wherein the means comprises at least one of a rack and gear mechanism, a lead screw and nut mechanism, and a linear rail and slide mechanism.

4. The surgical retractor of claim 3, further comprising a locking element.

5. The surgical retractor of claim 3, wherein the retractor handle comprises an elongate shape having a length aligned with the operational axis, the elongate shape comprising a substantially circular cross section having a circle center positioned on the operational axis, and
    wherein the means for moving the second blade relative to the elongate element comprises a driver handle, and wherein the driver handle comprises a driver handle elongate shape having a driver handle length positioned orthogonal to the operational axis, the driver handle elongate shape comprising a substantially circular cross section having a driver handle circle center positioned on a driver handle axis aligned with the drive handle length, wherein rotation of the driver handle about the driver handle axis activates movement of the second blade relative to the elongate element.

6. The surgical retractor of claim 1, wherein when the guide element is received in the opening, the guide element is located along a second blade exterior surface.

7. The surgical retractor of claim 1, wherein the guide element comprises a dissector.

8. The surgical retractor of claim 1, wherein at least one of the first blade and the second blade define a channel, wherein the channel is configured to receive at least partially at least one of a shim, a K-wire, a light source, a probe, and a support frame.

9. The surgical retractor of claim 1, wherein at least one of the first arm and second arm comprises a connection element for connecting the arm to an articulating arm, wherein said connection element is positioned on the arm at a position between the elongate element and the respective upper portion of the respective blade portion secured to the arm.

10. A surgical retractor comprising:
    an elongate element comprising an elongate element distal end and an elongate element proximal end with a length therebetween, the elongate element defining an operational axis along the length thereof, a retractor handle secured to the elongate element proximal end;

a first blade having a first upper portion secured to a first arm extending from the elongate element distal end and a first blade portion comprising a first blade face, wherein the first arm is configured to move along the length of the elongate element, wherein the first blade defines a reference point located thereon, and wherein a movement of the first arm along the length of the elongate element moves the reference point in a linear direction parallel to the operational axis, wherein movement of the first arm along the length of the elongate element moves the first arm relative to the retractor handle and relative to a second arm, wherein the first blade further comprises an opening along a length of the first blade and through the first upper portion; and a second blade having a second upper portion secured to a second arm extending from the elongate element and a second blade portion having a second blade face that faces the first blade face and an exterior surface opposite the second blade face, wherein the second arm is positioned along the length of the elongate element at a position between the retractor handle and the first arm, wherein the second blade further comprises an opening along a length of the second blade and through the second upper portion, wherein the opening of the first blade and the opening of the second blade is dimensioned to receive a guide element therethrough such that surgical retractor is advanceable to a surgical target site with the first blade portion and second blade portion located on the same side of the guide element.

11. The surgical retractor of claim 10, further comprising means for moving either the first blade or the second blade relative to the elongate element.

12. The surgical retractor of claim 11, wherein the means comprises at least one of a rack and gear mechanism, a lead screw and nut mechanism, and a linear rail and slide mechanism.

13. The surgical retractor of claim 12, further comprising a locking element.

14. The surgical retractor of claim 12, wherein the retractor handle comprises an elongate shape having a length aligned with the operational axis, the elongate shape comprising a substantially circular cross section having a circle center positioned on the operational axis, and wherein the means for moving the second blade relative to the elongate element comprises a driver handle, and wherein the driver handle comprises a driver handle elongate shape having a driver handle length positioned orthogonal to the operational axis, the driver handle elongate shape comprising a substantially circular cross section having a driver handle circle center positioned on a driver handle axis aligned with the drive handle length, wherein rotation of the driver handle about the driver handle axis activates movement of the second blade relative to the elongate element.

15. The surgical retractor of claim 10, wherein when the guide element is received in the opening of the first blade or the opening of the second blade, the guide element is located along either a first blade exterior surface or a second blade exterior surface.

16. The surgical retractor of claim 10, wherein the guide element comprises a dissector.

17. The surgical retractor of claim 10, wherein at least one of the first blade and the second blade define a channel, wherein the channel is configured to receive at least partially at least one of a shim, a K-wire, a light source, a probe, and a support frame.

18. The surgical retractor of claim 10, wherein at least one of the first arm and second arm comprises a connection element for connecting the arm to an articulating arm, wherein said connection element is positioned on the arm at a position between the elongate element and the respective upper portion of the respective blade portion secured to the arm.

* * * * *